(12) United States Patent
Weber (10) Patent No.: US 6,896,686 B2
(45) Date of Patent: May 24, 2005

(54) ARTHROSCOPIC SUTURE PASSING INSTRUMENT

(75) Inventor: Robert M. Weber, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 328 days.

(21) Appl. No.: 10/102,743

(22) Filed: Mar. 22, 2002

(65) Prior Publication Data

US 2002/0138084 A1 Sep. 26, 2002

Related U.S. Application Data (60) Provisional application No. 60/278,004, filed on Mar. 23, 2001.

(51) Int. Cl.$^7$ .............................................. A61B 17/04
(52) U.S. Cl. ..................... 606/145; 606/144; 606/139; 606/148; 606/185; 606/223
(58) Field of Search ................................ 606/1, 53, 60, 606/72, 139–150, 167, 170, 185, 205–212, 222–233; 604/272; 128/898

(56) References Cited

U.S. PATENT DOCUMENTS

| | | | |
|---|---|---|---|
| 4,923,461 A | 5/1990 | Caspari et al. | |
| 4,957,498 A | 9/1990 | Caspari et al. | |
| 5,059,201 A | 10/1991 | Asnis | |
| 5,522,820 A | 6/1996 | Caspari et al. | |
| 5,728,107 A | 3/1998 | Zlock et al. | |
| 5,730,747 A | 3/1998 | Ek et al. | |
| 5,947,982 A | 9/1999 | Duran | |
| 5,980,538 A | * 11/1999 | Fuchs et al. | ................. 606/145 |
| 6,051,006 A | 4/2000 | Shluzas et al. | |
| 6,183,484 B1 | 2/2001 | Matsutani et al. | |
| 6,511,487 B1 | * 1/2003 | Oren et al. | ................. 606/145 |
| 2003/0065337 A1 | * 4/2003 | Topper et al. | ............... 606/144 |
| 2003/0220658 A1 | * 11/2003 | Hatch et al. | ................. 606/139 |

FOREIGN PATENT DOCUMENTS

| | | | | |
|---|---|---|---|---|
| DE | 3136083 | * | 3/1983 | ................. 606/145 |
| DE | 198 07 743 | | 6/1999 | |

* cited by examiner

*Primary Examiner*—Glenn K. Dawson
(74) *Attorney, Agent, or Firm*—Dickstein Shapiro Morin & Oshinsky LLP (57) ABSTRACT

An instrument for arthroscopic suture passing having a shaft with a proximal end and a distal end. A jaw disposed on the distal end has a needle and a hook. The jaw opens and closes with respect to a stationary distal tip of the instrument. A handle disposed on the proximal end manipulates the jaw. A movable suture shuttle is disposed in the distal tip of the instrument. Arthroscopic suture passing takes place by initially loading a length of suture into the suture shuttle, and capturing the suture by moving the suture shuttle away from a position in which it would engage the needle and hook. The needle then is advanced through tissue using the handle to close the jaw against the stationery tip. The suture shuttle then is advanced to load the suture onto the hook. Opening the jaw draws the needle back through the tissue, pulling the suture in a loop through the tissue. A spring arm urges tissue off of the needle. The loop of suture then is available for further suturing or knot tying.

20 Claims, 13 Drawing Sheets

ARTHROSCOPIC SUTURE PASSING INSTRUMENT

This application claims the benefit of U.S. Provisional Patent Application Ser. No. 60/278,004 filed Mar. 23, 2001.

BACKGROUND OF THE INVENTION

1. Field of the Invention

The present invention relates to a surgical suture passing instrument, and more specifically to a hand instrument for passing suture in arthroscopic tissue repair procedures.

2. Brief Description of the Related Art

Arthroscopic reattachment, of a rotator-cuff tendon for example, often requires the surgeon generally to attach a length of suture material remotely to an internal body part, and then to secure the suture to another part. In a typical example, suture is passed through a detached tendon and is then secured to a hole or anchor in a bone. Various instruments have been developed for this purpose. U.S. Pat. No. 5,522,820 to Caspari describes a suture instrument that has a pair of relatively-movable jaws. A piercing needle with a hook is fixed to one of the jaws. The other jaw holds a length of suture. When the jaws are closed together, the needle pierces the tissue between them. The suture is picked up by the hook end of the needle and pulled back through the tissue as the jaws are opened. This instrument is relatively bulky, which is disadvantageous for arthroscopic surgery. In addition, the instrument has no independent control over whether the suture engages the hook once the jaws are closed.

SUMMARY OF THE INVENTION

An arthroscopic suturing instrument which overcomes the disadvantages of the prior art is provided. The instrument includes a shaft having a proximal end and a distal end. A jaw disposed on the distal end takes the form of a needle with a hook. The jaw opens and closes in relation to the distal end of the shaft. A handle disposed on the proximal end of the shaft operates to open and close the jaw. When the jaw is closed, the needle and hook are received in an opening in the distal end of the shaft.

A slidable suture shuttle is provided on the distal end portion of the shaft. Movement of the shuttle is controlled by a trigger near the handle, which moves the shuttle distally and proximally to open and close an associated slot for holding a length of suture. The shuttle is moved proximally to hold the suture held in the slot away from the needle's hook while the jaw is closed and tissue is pierced with the needle. A spring arm pivots into place to hold the tissue. The trigger then is pulled and the shuttle loads the suture distally into the hook. Opening the jaw then draws the suture out of the slot and through the tissue in the form of a loop captured by the hook. The spring arm serves to urge the tissue off of the needle. Arthroscopic suture passing begins by loading a length of suture into the slot on the suture shuttle. The suture shuttle and the suture then are moved away from a position of engagement with the needle and hook using the trigger. The operative distal end of the instrument is advanced toward tissue to be repaired, and the needle is pressed through tissue by closing the jaw using the instrument handles. The suture shuttle is moved back into position so as to load the suture onto the hook. Opening the jaw and withdrawing the needle from the tissue pulls a loop of suture through the tissue, which is then available for further suturing or knot tying.

Other features and advantages of the present invention will become apparent from the following description of the invention which refers to the accompanying drawings.

DETAILED DESCRIPTION OF EMBODIMENTS OF THE INVENTION

Figure 1:
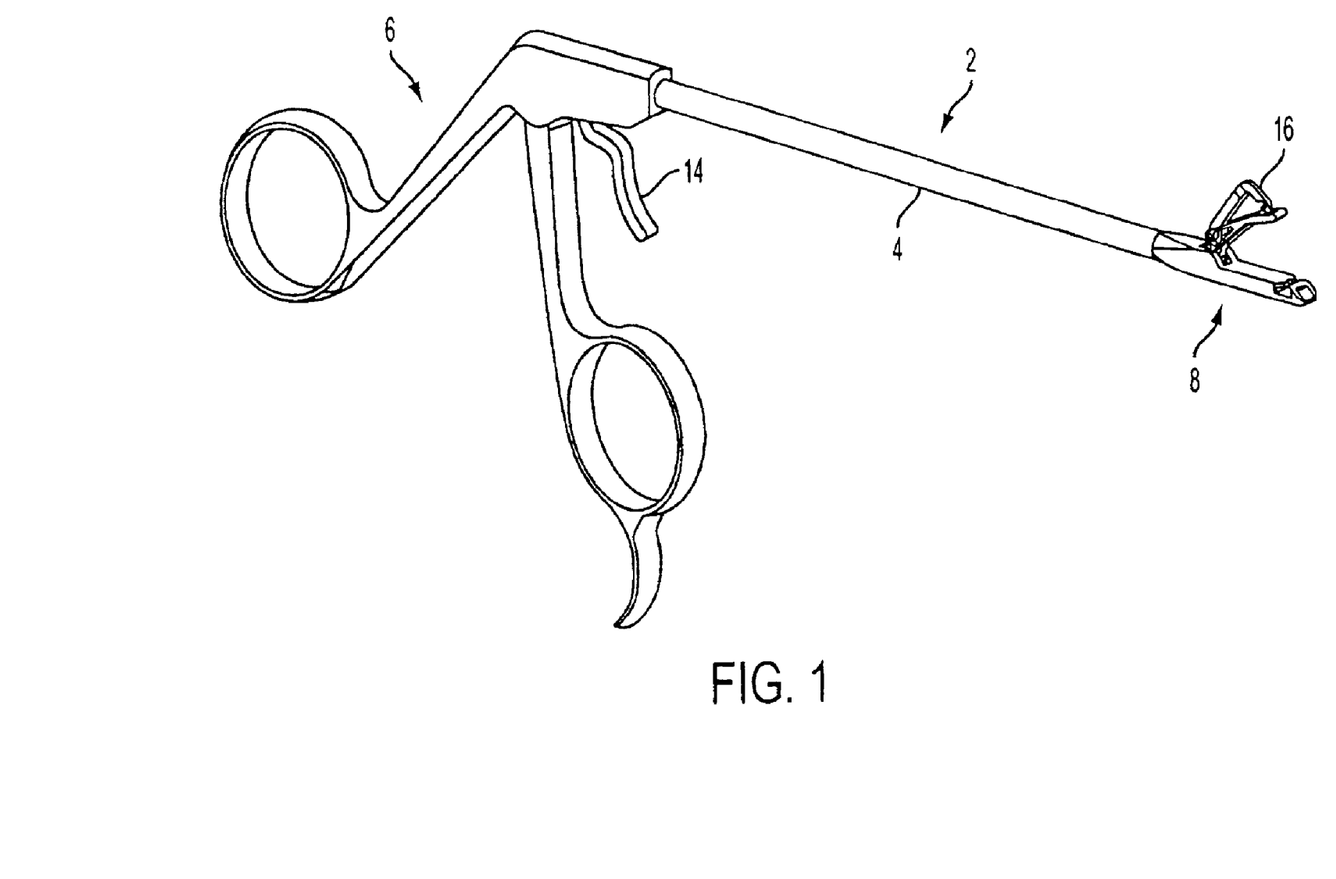
FIG. 1 is a perspective view of a suture passing instrument according to a preferred embodiment of the present invention.

Referring initially to FIG. 1, a preferred embodiment of an arthroscopic suture passing instrument 2 according to the present invention is shown in a perspective view. Hand instrument 2 includes a shaft 4 connecting a handle 6 disposed proximally to an operative jaw 8 disposed distally.

Figure 2:
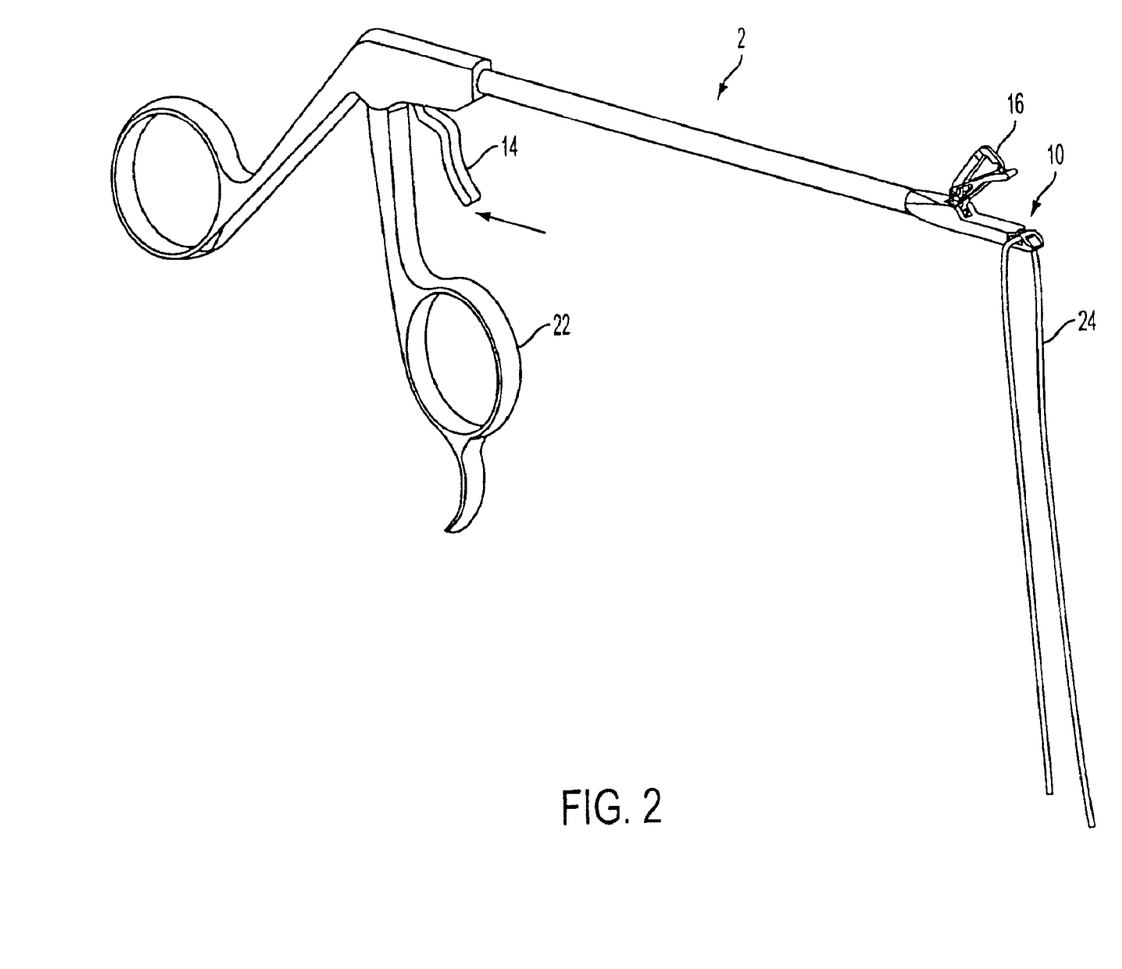
FIG. 2 is a perspective view of the suture passing instrument of FIG. 1 in an initial step of loading suture into the instrument.
Figure 3:
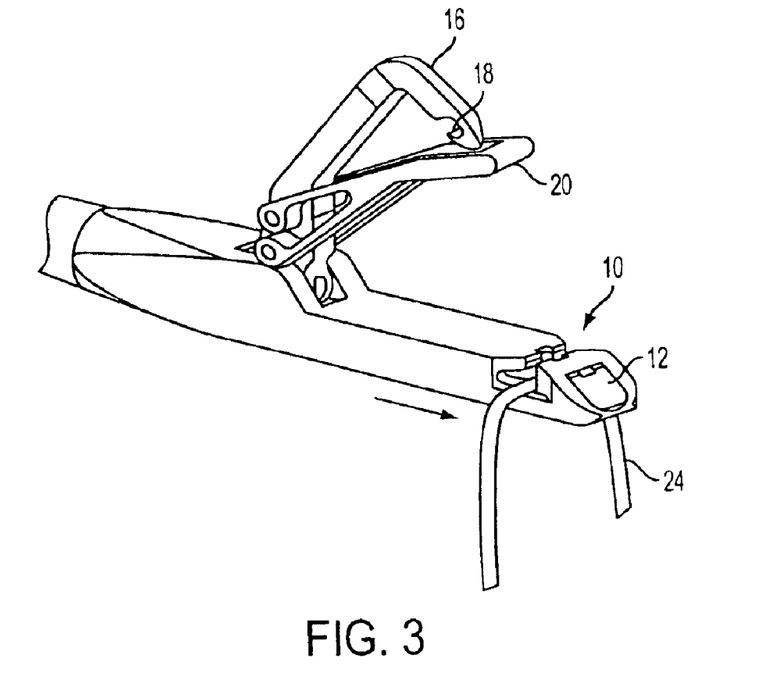
FIG. 3 is a close up of the distal tip of the suture passing instrument as shown in FIG. 2.

Referring also to FIGS. 2 and 3, hand instrument 2 includes a slot 10 formed at the distal end. A slidable suture shuttle 12, shown in a forward position in FIG. 3, controls access to slot 10. Suture shuttle 12 is operated using trigger 14, which is connected to the suture shuttle by a control rod (not shown), for example.

The structure and function of the suture shuttle will be explained in more detail below in connection with a preferred method of suture passing according to the present invention.

Figure 4:
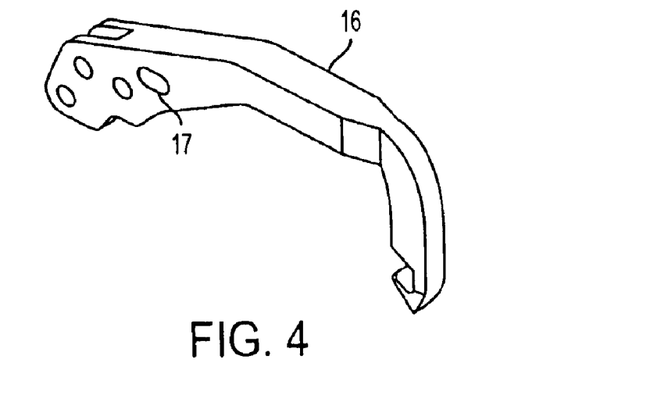
FIG. 4 is a detail elevation view of a needle hook according to the present invention.

Operative jaw 8 includes a needle 16. A hook 18 is formed toward the pointed tip of needle 16. A spring arm 20 pivots to urge tissue off of needle 16 as the jaws are opened by way of finger handle 22. Spring arm 20 preferably is Y shaped when viewed in elevation, and during manufacture of the instrument, is flexed slightly before being pinned into place on needle 16 to provide a load on the spring arm. The spring arm pivots around the bottom pin, while the top hole 17 is a horizontally oriented oval opening through needle 16 as shown in FIG. 4. The oval opening allows some sliding as the jaw closes, such that the spring arm swings in place to hold the tissue as the operative jaw is closed, and urges tissue off the end of the needle as the jaw is opened.

In a first step of suturing using the instrument 2, slot 10 in the stationary tip of instrument 2 is moved into an open position by pulling back on trigger 14, as shown by the directional arrow in FIG. 2. As a result, suture shuttle 12 slides into a forward position as shown by the directional arrow in FIG. 3. A length of suture 24 now can be placed in slot 10.

Figure 5:
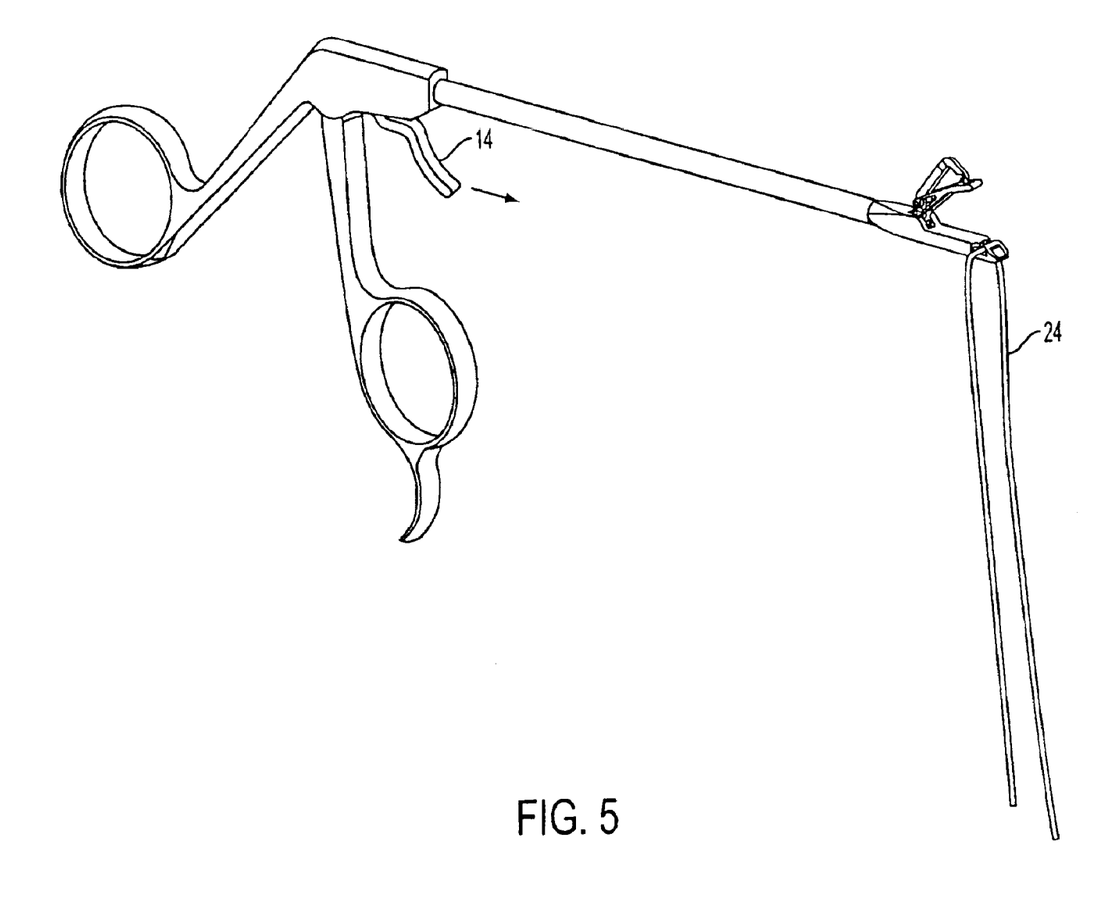
FIG. 5 is a perspective view of the suture passing instrument and illustrates a subsequent suture loading step in the method of suturing according to the present invention.
Figure 6:
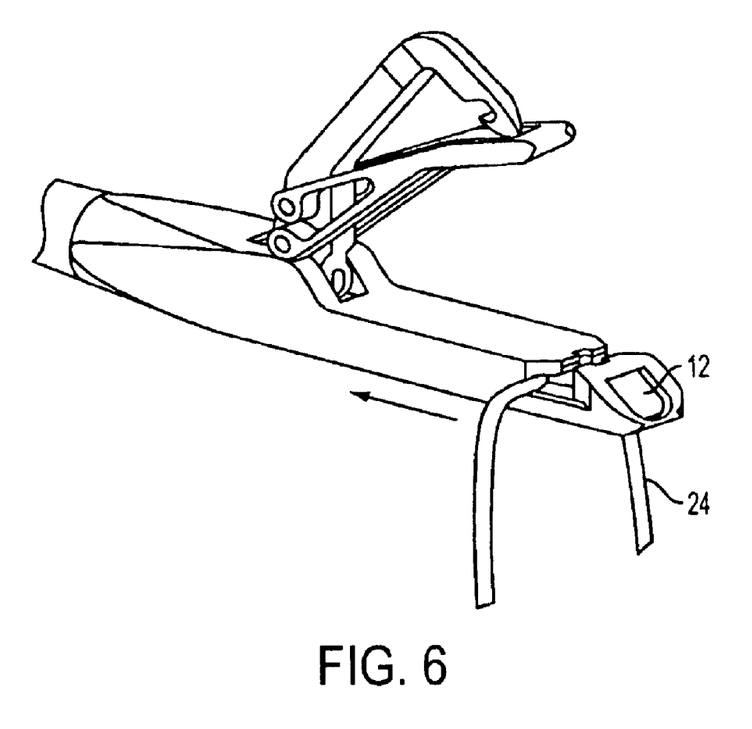
FIG. 6 is a close up of the distal tip of the suture passing instrument as shown in FIG. 4.

Referring to FIGS. 5 and 6, pushing trigger 14 forward in the direction of the arrow shown in FIG. 5 slides the suture shuttle back in the direction of the arrow shown in FIG. 6. As a result, suture 24 is withdrawn away from the slot 10, to be replaced by an opening through which needle 16 can pass.

Figure 7:
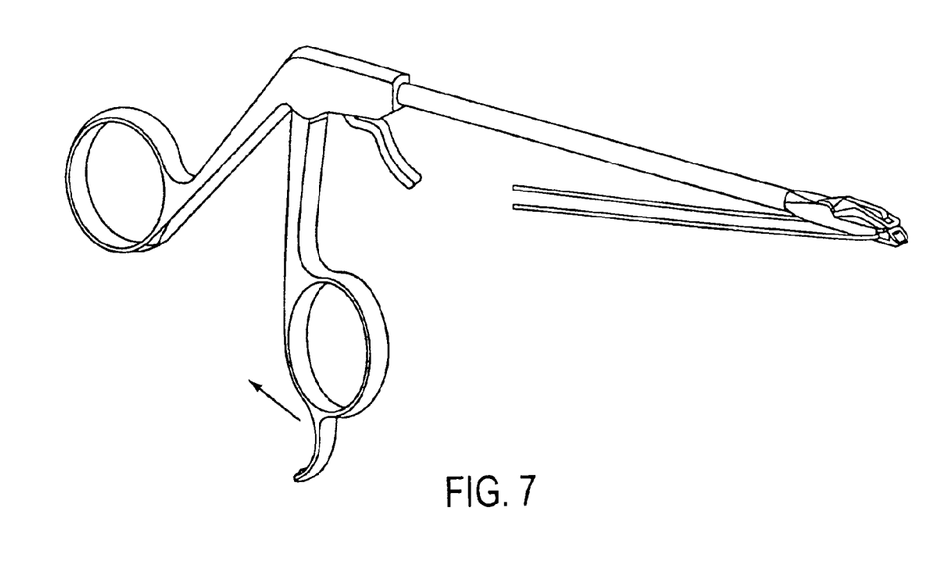
FIG. 7 is a perspective view of the suture passing instrument in condition for insertion through a cannula in the method of suturing according to the present invention.
Figure 8:
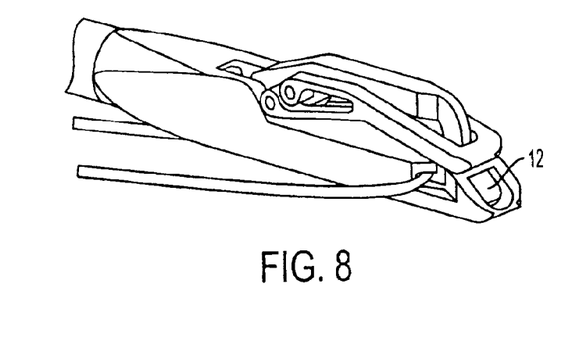
FIG. 8 is a close up of the distal tip of the suture passing instrument as shown in FIG. 7.

Referring to FIGS. 7 and 8, operative jaw 8 is shown in a closed position. Jaw 8 is closed by operating finger handle 22 as indicated by the directional arrow in FIG. 7. As the jaw closes, needle 16 passes through an opening in shuttle 12. In this closed position, the operative end of the instrument can be passed through an arthroscopic cannula.

Figure 9:
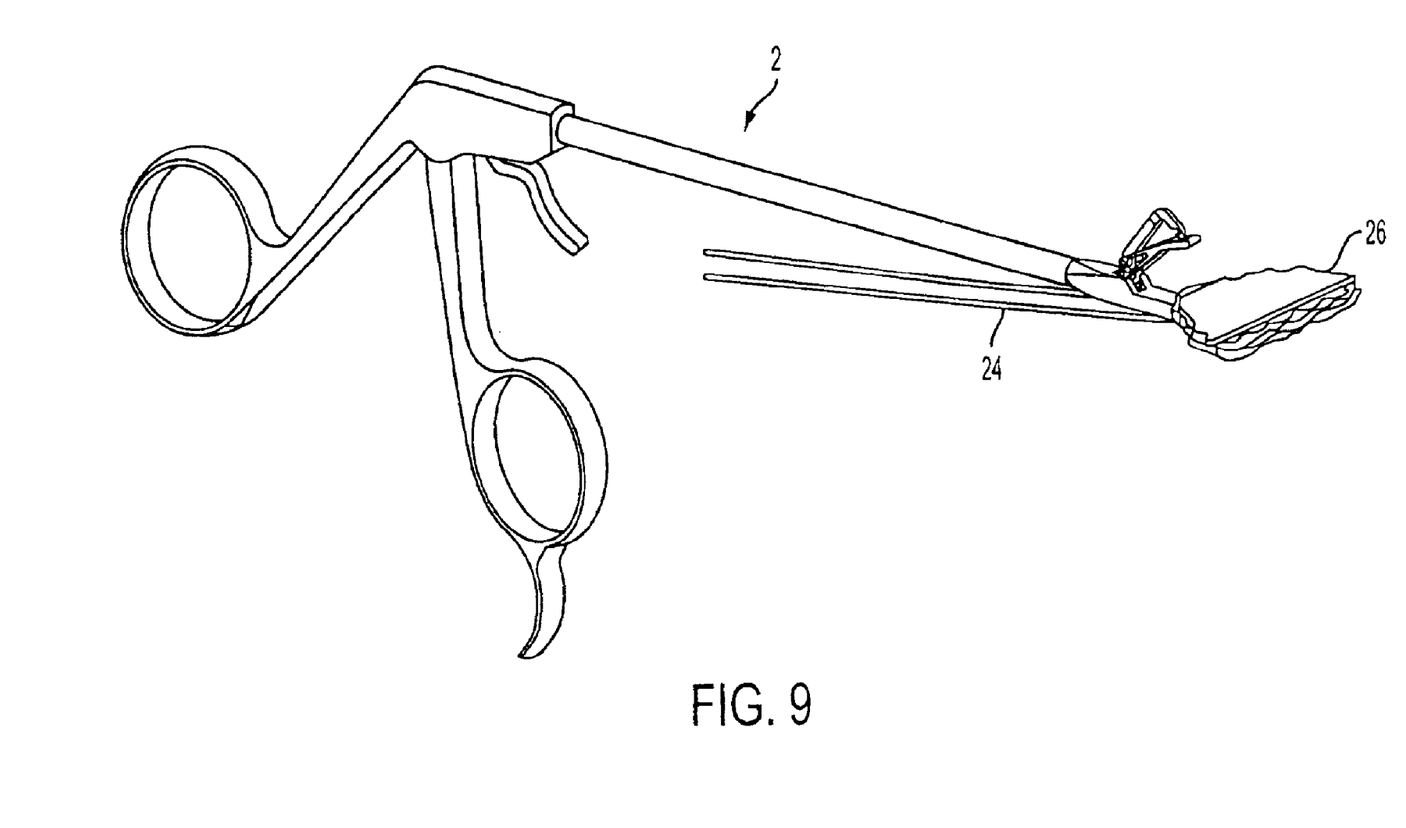
FIG. 9 is a perspective view of the suture passing instrument and illustrates a step of proximating tissue in a method of suturing according to the present invention.
Figure 10:
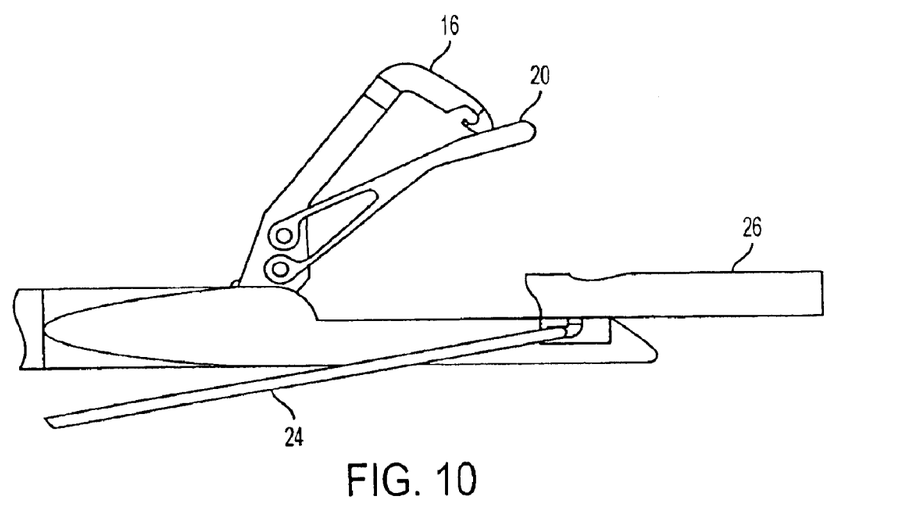
FIG. 10 is a close up in elevation of the distal tip of the suture passing instrument as shown in FIG. 9.
Figure 11:
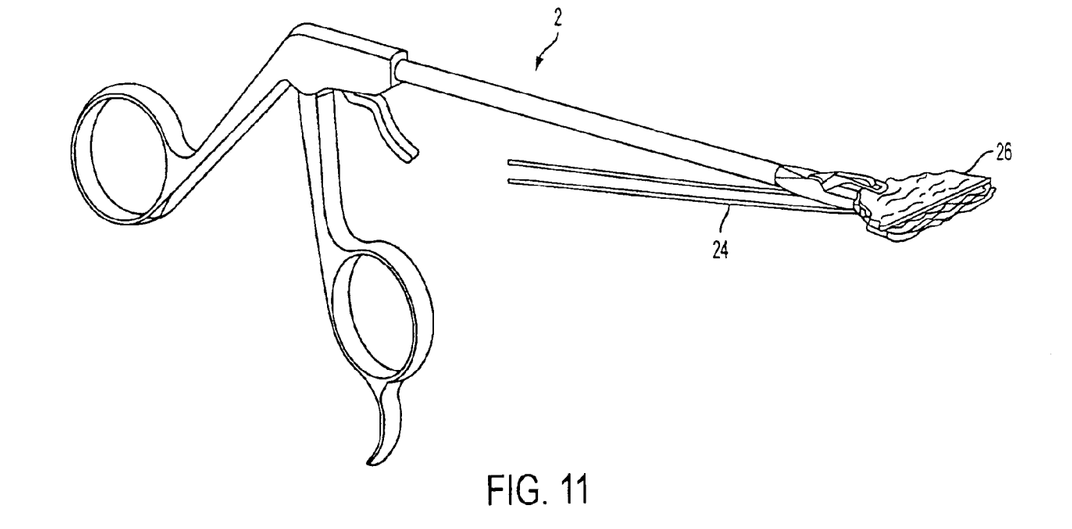
FIG. 11 is a perspective view of a suture passing instrument and illustrates a step of piercing tissue in the method of suturing according to the present invention.
Figure 12:
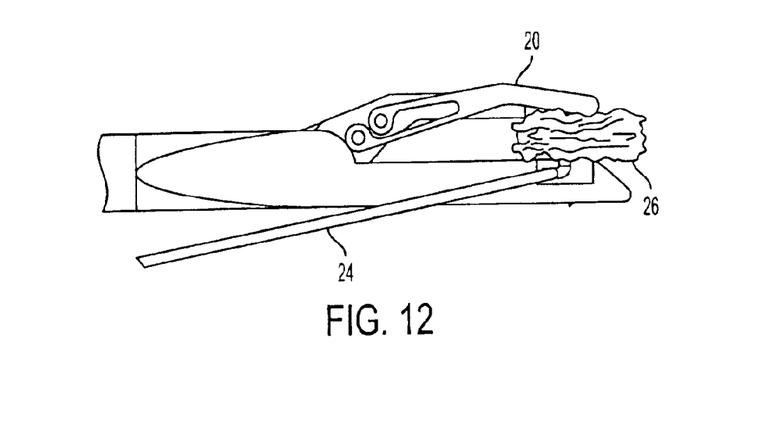
FIG. 12 is a close up in elevation of the tip of the suture passing instrument as shown in FIG. 11.
Figure 13:
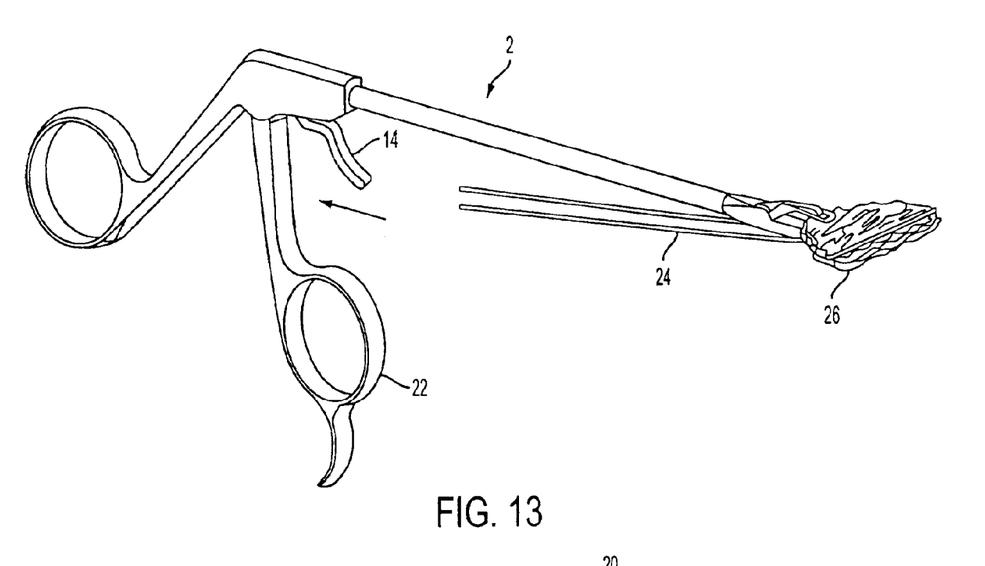
FIG. 13 is a perspective view of the suture passing instrument with the suture shuttle advanced to the forward position.
Figure 14:
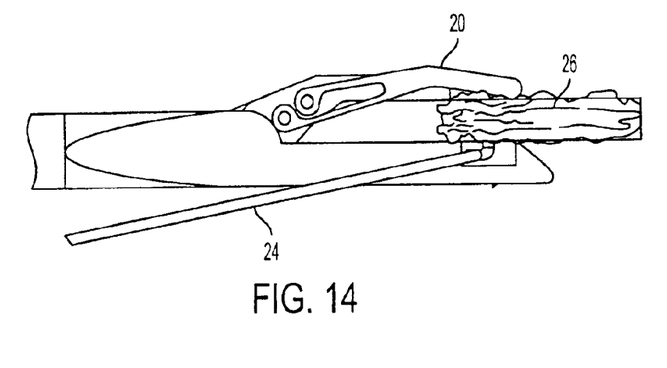
FIG. 14 is a close up view in elevation of the tip of the suture passing instrument as shown in FIG. 13 with the suture shuttle in the forward position.

Referring to FIGS. 9 and 10, hand instrument 2 has been loaded with suture and is positioned proximate a section of tissue 26 in need of repair. In FIGS. 11 and 12, operative jaw 8 is closed. Needle 16 pierces tissue 24. In FIGS. 13 and 14, with the jaw in the closed position, trigger 14 is pulled back as indicated by the arrow in FIG. 13, to move shuttle 12 forward and load suture 24 into hook 18. Hook 18 preferably includes a barb which defines a notch for holding the loop of suture during retraction of the needle.

Figure 15:
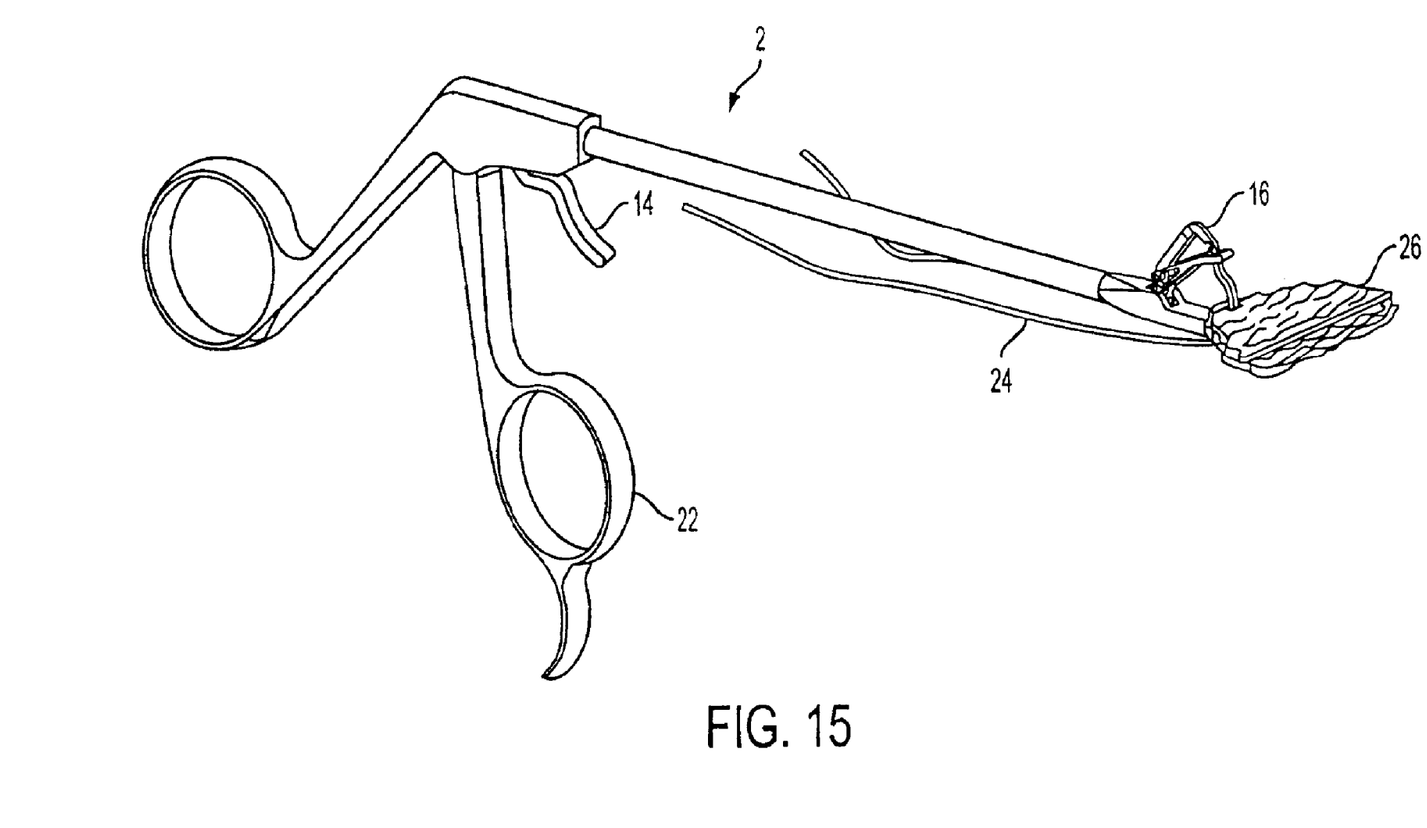
FIG. 15 is a perspective view of the suture passing instrument illustrating a step of drawing a loop of suture through the tissue according to the present invention.
Figure 16:
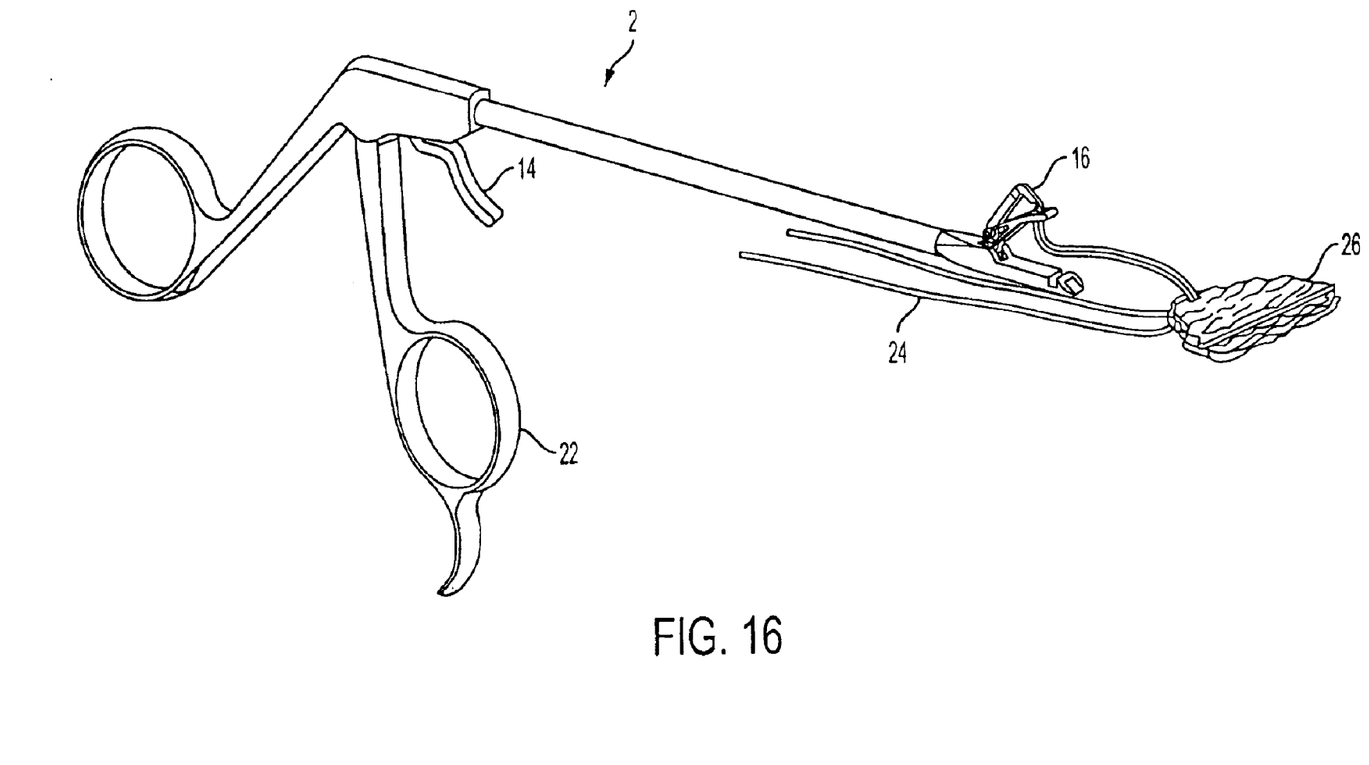
FIG. 16 is a perspective view of the suture passing instrument in retrograde from the tissue and pulling the suture loop formed through the tissue.
Figure 17:
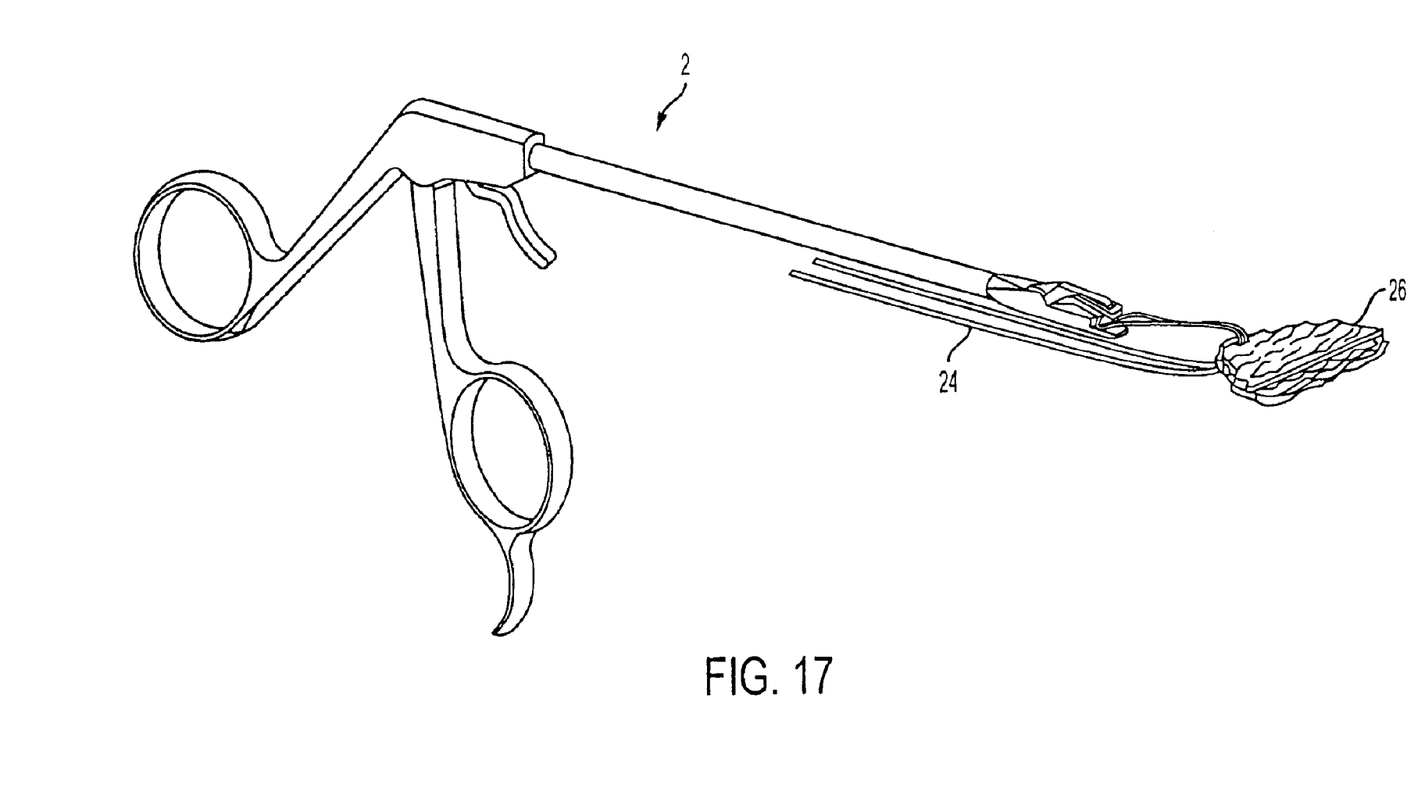
FIG. 17 is a perspective view of the suture passing instrument in a closed position ready for withdrawal through the arthroscopic cannula.

By opening the jaw using finger handle 22, the hooked suture 24 is drawn back through the tissue, forming a loop of the suture through the tissue, as shown in FIG. 15. As the instrument is withdrawn, the suture loop is pulled through tissue 26, as shown in FIG. 16. The operative jaw then is closed again, as shown in FIG. 17, for withdrawal from the operative site out through the cannula.

Slot 10 includes a lateral opening for accepting suture, and a longitudinal opening into which the hook-end of needle 16 fits. Preferably, bevels are formed on either side of the suture slot to provide relief clearances for the suture strand. The forward end of the instrument preferably is rounded for ease of insertion and atraumatic operation.

Although the present invention has been described in relation to particular embodiments thereof, many other variations and modifications and other uses will become apparent to those skilled in the art. Accordingly, the present invention be limited not by the specific disclosure herein, but only by the appended claims.

What is claimed is:

1. An instrument for arthroscopic suture passing, the instrument comprising:
   a shaft having a proximal end and a distal end;
   a jaw disposed distally on the shaft and having a needle and a hook;
   a handle disposed proximally on the shaft for manipulating the jaw; and
   a movable suture shuttle disposed on the distal end of the shaft.

2. The instrument of claim 1, further comprising a spring arm associated with the needle for urging tissue away from the needle.

3. The instrument of claim 1, wherein the shuttle includes a slot for holding suture.

4. The instrument of claim 1, wherein the shuttle has an open position in which suture can be accepted by the shuttle.

5. The instrument of claim 1, wherein the shuttle has a closed position in which suture accepted by the shuttle is prevented from engaging the hook.

6. The instrument of claim 1, wherein the shuttle is operated between the open position and the closed position by way of a trigger.

7. The instrument of claim 1, further comprising a operatively connected to the movable suture shuttle.

8. The instrument of claim 7, wherein the trigger is disposed on the handle.

9. The instrument of claim 1, wherein the distal end of the shaft has a width greater than a width of the needle, the distal end of the shaft having an opening that provides a clearance through which at least a portion of the needle with the hook passes when the jaw is closed.

10. A method of arthroscopic suture passing using an instrument having:
    a shaft having a proximal end and a distal end;
    a jaw disposed on the distal end and having a needle and a hook;
    a handle disposed on the proximal end for manipulating the jaw; and
    a movable suture shuttle disposed in the tip of the shaft, the method comprising the steps of:
    loading a length of suture into the suture shuttle;
    moving the suture with the suture shuttle away from a position of engagement with the needle and hook;
    moving the distal end of the instrument toward tissue to be repaired;
    advancing the needle through tissue by closing the jaw;
    moving the suture shuttle so as to load the suture onto the hook; and
    opening the jaw and removing the needle from the tissue, thereby pulling the suture through the tissue.

11. The method of claim 10, wherein the suture shuttle includes a slot, and the step of loading a length of suture into the suture shuttle comprises placing the suture into the slot.

12. An instrument for arthroscopic suture passing, the instrument comprising:
    a shaft;
    a jaw supported on the shaft and having a needle with a hook;
    a handle operatively engaged to manipulate the jaw; and
    a shuttle arranged and configured to move a suture strand alternately between a position of engagement and a position of disengagement with the hook.

13. The instrument of claim 12, further comprising a spring arm operatively arranged and configured to urge tissue away from the needle.

14. The instrument of claim 13, wherein the spring arm is configured to urge tissue away from the needle as the jaw is opened.

15. The instrument of claim 13, wherein the spring arm is pivotally mounted on the needle.

16. The instrument of claim 12, wherein the shuttle includes an opening to which suture has access.

17. The instrument of claim 12, wherein the shuttle position of engagement exposes the shuttle to access by the suture.

18. The instrument of claim 12, wherein the shuttle position of disengagement exposes an opening through which the needle can pass.

19. The instrument of claim 12, further comprising a trigger operatively disposed to urge the shuttle between the positions of engagement and disengagement.

20. The instrument of claim 12, wherein the distal end of the shaft has a width greater than a width of the needle, the distal end of the shaft being provided with a clearance through which at least a portion of the needle with the hook passes when the jaw is closed.

* * * * *

UNITED STATES PATENT AND TRADEMARK OFFICE
CERTIFICATE OF CORRECTION

PATENT NO. : 6,896,686 B2 Page 1 of 1
APPLICATION NO. : 10/102743
DATED : May 24, 2005
INVENTOR(S) : Robert M. Weber et al.

It is certified that error appears in the above-identified patent and that said Letters Patent is hereby corrected as shown below:

On Front Page:

On the first page, at (75), as an inventor, please add --Stephen S. Burkhart, San Antonio, TX (US)--

Signed and Sealed this

Twenty-seventh Day of July, 2010

David J. Kappos
*Director of the United States Patent and Trademark Office*